United States Patent [19]

Doonan et al.

[11] 4,233,444

[45] Nov. 11, 1980

[54] CONTINUOUS PROCESS FOR THE PRODUCTION OF MONOALKALI METAL CYANURATES

[75] Inventors: David F. Doonan; Kurt H. Moller, both of Lake Charles, La.

[73] Assignee: Olin Corporation, New Haven, Conn.

[21] Appl. No.: 54,334

[22] Filed: Jul. 2, 1979

[51] Int. Cl.³ ............................................ C07D 251/32
[52] U.S. Cl. ................................................... 544/192
[58] Field of Search ..................... 544/192, 180, 219

[56] References Cited

U.S. PATENT DOCUMENTS

| | | | |
|---|---|---|---|
| 3,835,134 | 9/1974 | Schiessleod | 260/248 C |
| 3,835,135 | 9/1974 | Sawhill | 260/248 C |
| 3,846,424 | 11/1974 | Hirdler et al. | 544/192 |

*Primary Examiner*—John M. Ford
*Attorney, Agent, or Firm*—James B. Haglind; Donald F. Clements

[57] ABSTRACT

A continuous process is disclosed for the production of monoalkali metal cyanurates. In the process, cyanuric acid and an aqueous solution of the alkali metal hydroxide are continuously reacted in a first reactor to produce a first slurry comprised of cyanuric acid and a monoalkali metal cyanurate. This first slurry is conveyed to a second reactor to further react the cyanuric acid with the alkali metal hydroxide to produce a second slurry comprised of the monoalkali metal cyanurate.

The novel process produces slurries of monoalkali metal cyanurate which are consistent both with respect to chemical composition and solids content while reducing equipment and operating costs.

12 Claims, No Drawings

CONTINUOUS PROCESS FOR THE PRODUCTION OF MONOALKALI METAL CYANURATES

This invention relates to the manufacture of cyanuric acid derivatives. More particularly, this invention relates to the manufacture of monoalkali metal cyanurates.

In the production of chloroisocyanurate bleaches and sanitizing agents, an alkali metal cyanurate such as sodium cyanurate is reacted with a chlorinating agent such as chlorine or hypochlorous acid. While disodium cyanurate or trisodium cyanurate are frequently used, monosodium cyanurate is preferred because of its ease of preparation. In addition, monosodium cyanurate slurries have lower viscosities and can be more easily handled at high concentrations.

Processes for chlorinating monoalkali metal cyanurates to produce dichloroisocyanuric acid and trichloroisocyanuric acid are described in U.S. Pat. No. 3,835,134, issued Sept. 10, 1974, to H. W. Schiessl et al and U.S. Pat. No. 3,835,135, issued Sept. 10, 1974, to D. L. Sawhill.

In these processes, monoalkali metal cyanurates such as monosodium cyanurate are produced by reacting cyanuric acid with a sodium hydroxide solution in a batch process. While a batch process satisfactorily produces a monoalkali metal cyanurate product, considerable operator attention is required to produce slurries in which undesired agglomeration is minimized and which are consistent with respect to their chemical composition. In addition, capital costs for reaction vessels are considerably higher.

It is an object of the present invention to provide a continuous process for producing monoalkali metal cyanurates.

Another object of the present invention is to provide a continuous process for producing monoalkali metal cyanurates having a uniform chemical composition.

An additional object of the present invention is to provide a continuous process for producing monoalkali metal cyanurates at reduced operating and capital costs.

These and other objects of the invention are accomplished in a continuous process for producing a monoalkali metal cyanurate which comprises:

(a) continuously feeding cyanuric acid and continuously feeding an aqueous solution of an alkali metal hydroxide to a first reactor, (b) continuously reacting cyanuric acid with the aqueous solution of alkali metal hydroxide to produce a first slurry comprised of cyanuric acid and a monoalkali metal cyanurate, (c) continuously conveying a portion of the first slurry to a second reactor, (d) continuously admixing the portion of the first slurry to further react the cyanuric acid with the alkali metal hydroxide to produce a second slurry comprised of a monoalkali metal cyanurate, and recovering said monoalkali metal cyanurate.

More in detail, the novel process of the present invention produces monoalkali metal cyanurates including monosodium cyanurate, monopotassium cyanurate, and monolithium cyanurate.

In producing these compounds, cyanuric acid is employed as one of the reactants. Cyanuric acid is commercially available in powder (e.g. $-100$ to $+300$ mesh) or granular (e.g. $-20$ to $+100$ mesh) forms. Also suitably used are slurries or cakes of cyanuric acid which are produced as required using, for example, processes described in U.S. Pat. No. 2,943,088, issued June 28, 1960, to R. H. Westfall; U.S. Pat. No. 3,008,961, issued November 14, 1961, to B. H. Wojcik; U.S. Pat. No. 3,297,697, issued Jan. 10, 1967, to J. B. Reynolds et al; or U.S. Pat. No. 3,635,968, issued to H. Goelz et al. Preferably a wet cake of cyanuric acid recovered from a filter or centrifuge is used as the reactant where the cake contains from about 65 to about 99 and preferably from about 70 to about 85 percent by weight of cyanuric acid.

In the process of the present invention, the cyanuric acid is reacted with an aqueous solution of an alkali metal hydroxide such as sodium hydroxide, potassium hydroxide, or lithium hydroxide. Concentrations of the alkali metal hydroxide in the solutions are in the range of from about 1 to about 30, and preferably from about 4 to about 20 percent by weight. Sufficient amounts of the alkali metal hydroxide are reacted with the cyanuric acid to produce a first slurry comprising monoalkali metal cyanurate and cyanuric acid in the solid phase. Solids content of the first slurry is from about 4 to about 40, preferably from about 5 to about 25, and more preferably from about 8 to about 16 percent by weight of the slurry. While any suitable amount of monoalkali metal cyanurate may be present in the first slurry, it is preferred that the solid phase contain from about 70 to about 90 percent by weight of alkali metal cyanurate; the remainder of the solids being cyanuric acid. The reactants are continuously mixed during the reaction period. The density of the first slurry is maintained in the range of from about 1.02 to about 2.00, preferably from about 1.05 to about 1.20, and more preferably from about 1.07 to about 1.10 grams per milliliter by controlling the addition of the alkali metal hydroxide solution.

A portion of this first slurry is continuously conducted to a second reactor to permit the reaction to go to completion.

In one embodiment, at least stoichiometric amounts of the alkali metal hydroxide solution are fed to the first reactor so that the first slurry contains free alkali metal hydroxide. In the second reactor, this free alkali metal hydroxide reacts with the cyanuric acid present to completely convert the cyanuric acid to monoalkali metal cyanurate.

A preferred embodiment reacts less than stoichiometric amounts of alkali metal hydroxide solution in the first stage and adds additional alkali metal hydroxide to the second reactor to complete the reaction.

During this second stage of the process, the pH of the reaction mixture is maintained in the range of from about 8.5 to about 9.5, and preferably from about 8.9 to about 9.1, for example, by the controlled rate of addition of the alkali metal hydroxide. The second slurry produced is comprised of monoalkali metal cyanurate as the solid phase and a solution of monoalkali metal cyanurate as the liquid phase.

Residence time in the two reactors is determined previously by the particle size of the cyanuric acid used, coarse particles taking longer to dissolve and react. The reaction rate varies directly with the reciprocal of the particle size according to the following formula:

$$R = 6.0 \times 10^{-3} + (7.5 \times 10^{-5}/d)$$

where R is the reaction rate in minutes $^{-1}$ and d is the mean particle size of the cyanuric acid in inches.

Suitable cyanuric acid particle sizes in the process of the present reaction are those where d is from about 0.002 to about 0.01 and preferably from about 0.004 to about 0.006 of an inch.

The novel process of the present invention does not require heating or cooling in either stage of the reaction as the reaction is suitably conducted at ambient temperatures. However, the reaction mixture may be heated to increase the rate of reaction if desired.

The monoalkali metal cyanurate slurry produced by the novel process of the present invention may be used directly in the production of chloroisocyanurates such as dichloroisocyanuric acid, trichloroisocyanuric acid, or sodium dichloroisocyanurate. If desired, the slurry may be filtered to remove excess liquid.

Where the monoalkali metal cyanurate is to be used, for example, as the stabilizer for chlorine-containing water supplies such as swimming pools, the slurry is, for example, centrifuged and the monoalkali metal cyanurate recovered by flash drying the wet cake.

The novel process of the present invention achieves the continuous production of monoalkali metal cyanurate at reduced equipment and operating costs. In addition, the slurries produced are more consistent both with respect to chemical composition and solids content than can be achieved in a batch process.

The process of the present invention is further illustrated by the following Example. All percentages used are by weight unless otherwise specified.

EXAMPLE

A 2-liter reactor equipped with an agitator and having an overflow at the 1-liter level was fed continuously with cyanuric acid powder (0.004 inch) at the rate of 128 grams per hour. Also continuously fed to the reactor was a 4.5 percent sodium hydroxide solution at the rate of 853 milliliters per hour. During the retention period (1.2 hours) a milk-like slurry containing monosodium cyanurate, cyanuric acid, and sodium hydroxide was formed at ambient temperatures and without requiring cooling. The slurry had a viscosity of 85 cps, a density of 1.07 grams per milliliter, and a solids content of 14 percent of which about 80 percent was monosodium cyanurate. The slurry overflowed into a second 2-liter reactor fitted with an agitator, a pH electrode, and an overflow at the 1-liter level. The pH of the slurry in the second reactor was controlled at 9.0 by adjusting the NaOH flow to the first reactor. Conversion of cyanuric acid to monosodium cyanurate was complete as evidenced by the fact that the pH of the sample did not change on standing overnight. The slurry, uniform and free of large particles overflowed the second level and was used in the continuous preparation of trichloroisocyanuric acid.

What is claimed is:

1. A continuous process for producing a monoalkali metal cyanurate which comprises:
   (a) continuously feeding cyanuric acid and continuously feeding an aqueous solution of an alkali metal hydroxide to a first reactor,
   (b) continuously reacting said cyanuric acid and said aqueous solution of alkali metal hydroxide to produce a first slurry comprised of cyanuric acid and a monoalkali metal cyanurate,
   (c) continuously conveying a portion of said first slurry to a second reactor,
   (d) continuously admixing said portion of said first slurry to further react said cyanuric acid with alkali metal hydroxide to produce a second slurry comprised of said monoalkali metal cyanurate, and recovering said monoalkali metal cyanurate.

2. The process of claim 1 in which said alkali metal hydroxide is selected from the group consisting of sodium hydroxide, potassium hydroxide, and lithium hydroxide.

3. The process of claim 2 in which the density of said first slurry is in the range of from about 1.02 to about 2.00 grams per milliliter.

4. The process of claim 3 in which said aqueous solution has a concentration of from about 1 to about 30 percent by weight of said alkali metal hydroxide.

5. The process of claim 4 in which said first slurry has a solids content of from about 4 to about 40 percent by weight of said first slurry.

6. The process of claim 5 in which said solids content of said first slurry comprises from about 70 to about 90 percent by weight of monoalkali metal cyanurate; the balance of the solids content being cyanuric acid.

7. The process of claim 6 in which additional aqueous solution of alkali metal hydroxide is added to said second reactor to react with residual cyanuric acid in said portion of said first slurry.

8. The process of claim 7 in which said alkali metal hydroxide is sodium hydroxide.

9. The process of claim 8 in which the pH of said second slurry is maintained in the range of from about 8.5 to about 9.5.

10. The process of claim 9 in which said density of said first slurry is from about 1.05 to about 1.20 grams per milliliter.

11. The process of claim 10 in which said aqueous solution has a concentration of from about 4 to about 20 percent by weight of sodium hydroxide.

12. The process of claim 11 in which said pH of said second slurry is maintained at from about 8.9 to about 9.1.

* * * * *